US010670885B2

(12) United States Patent
Zhao

(10) Patent No.: US 10,670,885 B2
(45) Date of Patent: *Jun. 2, 2020

(54) OPHTHALMIC APPARATUS WITH CORRECTIVE MERIDIANS HAVING EXTENDED TOLERANCE BAND WITH FREEFORM REFRACTIVE SURFACES

(71) Applicant: Johnson & Johnson Surgical Vision, Inc., Santa Ana, CA (US)

(72) Inventor: Huawei Zhao, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,786

(22) Filed: Mar. 23, 2017

(65) Prior Publication Data

US 2017/0273778 A1    Sep. 28, 2017

Related U.S. Application Data

(60) Provisional application No. 62/312,321, filed on Mar. 23, 2016, provisional application No. 62/312,338, filed on Mar. 23, 2016.

(51) Int. Cl.
*A61F 2/16* (2006.01)
*G02C 7/06* (2006.01)
(Continued)

(52) U.S. Cl.
CPC ............ *G02C 7/061* (2013.01); *A61F 2/164* (2015.04); *A61F 2/1613* (2013.01);
(Continued)

(58) Field of Classification Search
CPC ......................... A61F 2/1645; G02C 2202/02
See application file for complete search history.

(56) References Cited

U.S. PATENT DOCUMENTS

| 2,077,092 A | 4/1937 | Broder |
| 3,305,294 A | 2/1967 | Alarez |

(Continued)

FOREIGN PATENT DOCUMENTS

| CN | 1035363 A | 9/1989 |
| CN | 1039487 A | 2/1990 |

(Continued)

OTHER PUBLICATIONS

International Search Report and Written Opinion for Application No. PCT/US2018/023946, dated Jun. 12, 2018, 16 pages.

(Continued)

*Primary Examiner* — David H Willse
*Assistant Examiner* — Javier G Blanco
(74) *Attorney, Agent, or Firm* — Johnson & Johnson Surgical Vision, Inc.

(57) ABSTRACT

The embodiments disclosed herein include improved toric lenses and other ophthalmic apparatuses (including, for example, contact lens, intraocular lenses (IOLs), and the like) that includes a freeform-polynomial surface area that establishes a band of operational meridian for the apparatus to an intended correction meridian. The freeform-polynomial surface area is defined by a mathematical expression comprising a combination of one or more polynomial expressions (e.g., Chebyshev-based polynomial expression, Zernike-based polynomial expression, etc.) each having a distinct complex orders.

23 Claims, 9 Drawing Sheets

(51) Int. Cl.
*G02C 7/04* (2006.01)
*G02C 7/02* (2006.01)

(52) U.S. Cl.
CPC .......... *A61F 2/1618* (2013.01); *A61F 2/1645* (2015.04); *A61F 2/1654* (2013.01); *G02C 7/021* (2013.01); *G02C 7/028* (2013.01); *G02C 7/041* (2013.01); *G02C 7/042* (2013.01); *G02C 7/044* (2013.01); *G02C 7/06* (2013.01); *A61F 2/1643* (2015.04); *A61F 2240/002* (2013.01); *A61F 2250/0097* (2013.01); *G02C 2202/02* (2013.01); *G02C 2202/06* (2013.01); *G02C 2202/10* (2013.01); *G02C 2202/20* (2013.01); *G02C 2202/22* (2013.01)

(56) References Cited

U.S. PATENT DOCUMENTS

| | | |
|---|---|---|
| 3,367,734 A | 2/1968 | Karl |
| 3,735,685 A | 5/1973 | Plummer |
| 4,010,496 A | 3/1977 | Neefe |
| 4,056,311 A | 11/1977 | Winthrop et al. |
| 4,162,122 A | 7/1979 | Cohen |
| 4,210,391 A | 7/1980 | Cohen et al. |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,173,723 A | 12/1992 | Volk et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,286,956 B1 | 9/2001 | Oyama et al. |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |

(56) References Cited

U.S. PATENT DOCUMENTS

| | | |
|---|---|---|
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,241,354 B2 | 8/2012 | Hong et al. |
| 8,740,382 B1 | 6/2014 | Liu et al. |
| 8,764,822 B2 | 7/2014 | Harris et al. |
| 8,862,447 B2 | 10/2014 | Weeber |
| 9,241,627 B2 | 1/2016 | Steinmueller |
| 9,393,108 B2 | 7/2016 | Canovas et al. |
| 9,491,431 B2 | 11/2016 | Zhou |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0021825 A1* | 2/2004 | Richardson ............. G02C 7/04 351/159.67 |
| 2004/0054358 A1 | 3/2004 | Cox |
| 2004/0068317 A1 | 4/2004 | Knight |
| 2004/0080710 A1 | 4/2004 | Wooley et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0055877 A1 | 3/2006 | Yanari |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0275929 A1 | 11/2009 | Zickler |
| 2009/0279048 A1 | 11/2009 | Hong et al. |
| 2009/0303465 A1 | 12/2009 | Clements et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0161048 A1 | 6/2010 | Schaper, Jr. |
| 2010/0220185 A1 | 9/2010 | Vertoprakhov et al. |
| 2010/0274234 A1 | 10/2010 | Liang |
| 2010/0315589 A1 | 12/2010 | Portney |
| 2011/0166652 A1 | 7/2011 | Bogaert et al. |
| 2011/0205486 A1 | 8/2011 | Zhao |
| 2012/0140166 A1 | 6/2012 | Zhao |
| 2012/0249955 A1 | 10/2012 | Sarver et al. |
| 2012/0310337 A1 | 12/2012 | Hacker et al. |
| 2012/0320334 A1 | 12/2012 | Ho et al. |
| 2013/0050637 A1 | 2/2013 | Roffman et al. |
| 2013/0307965 A1 | 11/2013 | Widman et al. |
| 2014/0016088 A1 | 1/2014 | De et al. |
| 2014/0135919 A1* | 5/2014 | Gontijo ............... A61F 2/1618 623/6.24 |
| 2014/0160436 A1 | 6/2014 | Kasthurirangan et al. |
| 2014/0268042 A1 | 9/2014 | Bor et al. |
| 2014/0293426 A1* | 10/2014 | Dobschal .......... G02B 27/0075 359/574 |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 | 11/2015 | Rosen et al. |
| 2015/0359625 A1 | 12/2015 | Argal et al. |
| 2015/0362746 A1 | 12/2015 | Skudder et al. |
| 2016/0157997 A1 | 6/2016 | Gerlach et al. |
| 2016/0299355 A1 | 10/2016 | Biemold et al. |

FOREIGN PATENT DOCUMENTS

| | | |
|---|---|---|
| CN | 1406120 A | 3/2003 |
| CN | 1833192 A | 9/2006 |
| CN | 102099729 A | 6/2011 |
| DE | 8107675 U1 | 7/1981 |
| DE | 3439551 A1 | 4/1986 |
| DE | 102005022683 A1 | 11/2006 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| EP | 2182891 B1 | 4/2014 |
| FR | 2745711 A1 | 9/1997 |
| JP | H0255314 A | 2/1990 |

(56) References Cited

FOREIGN PATENT DOCUMENTS

| | | |
|---|---|---|
| WO | 8603961 A1 | 7/1986 |
| WO | 9109336 A1 | 6/1991 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 9905499 A1 | 2/1999 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03009053 A1 | 1/2003 |
| WO | 2004034129 A1 | 4/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009076670 A1 | 6/2009 |
| WO | 2009105567 A1 | 8/2009 |
| WO | 2009137491 A1 | 11/2009 |
| WO | 2010009254 A1 | 1/2010 |
| WO | 2010009257 A1 | 1/2010 |
| WO | 2012083143 A1 | 6/2012 |
| WO | 2012085917 A1 | 6/2012 |
| WO | 2012154597 A1 | 11/2012 |
| WO | 2015022215 A1 | 2/2015 |
| WO | 2016123167 A1 | 8/2016 |

OTHER PUBLICATIONS

Abelman H., et al. "Tolerance and Nature of Residual Refraction in Symmetric Power Space as Principal Lens Powers and Meridians Change," Computational and Mathematical Methods in Medicine, 2014, vol. 2014, pp. 1-12.
Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.
Brown W.L., "Revisions to Tolerances in Cylinder Axis and in Progressive Addition Lens Power in ANSI Z80.1-2005," Optometry, 2006, vol. 77 (7), pp. 343-349.
Canovas C., et al., "Customized Eye Models for Determining Optimized Intraocular Lenses Power," Biomedical Optics Express, Jun. 1, 2011, vol. 2 (6), pp. 1649-1662.
International Search Report and Written Opinion for Application No. PCT/US2017/023772, dated Jul. 21, 2017, 14 pages.
International Search Report and Written Opinion for Application No. PCT/US2017/023864, dated Jul. 6, 2017, 15 pages.
International Search Report and Written Opinion for Application No. PCT/US2017/023888, dated Jul. 24, 2017, 14 pages.
International Search Report and Written Opinion for Application No. PCT/US2017/023897, dated Jul. 11, 2017, 17 pages.
Olsen T., "Simple Method to Calculate the Surgically Induced Refractive Change," Journal of Cataract & Refractive Surgery, Mar. 1993, vol. 19 (2), pp. 319-320.
Hill W., et al., "Monte Carlo Simulation of Expected Outcomes with the Acrysof Toric Intraocular Lens," BMC Ophthalmology, Oct. 2008, vol. 8, pp. 22.
International Preliminary Report on Patentability for Application No. PCT/US2017/023772, dated Oct. 4, 2018, 7 pages.
Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.
International Search Report and Written Opinion for Application No. PCT/US2017/023836, dated Jun. 19, 2017, 12 pages.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alio J.L., et al., "Phakic Anterior Chamber Lenses for the Correction of Myopia: A 7-Year Cumulative Analysis of complications in 263 Cases," Ophthalmology, Mar. 1999, vol. 106 (3), pp. 458-466.
Apple D.J., et al., "Anterior Chamber Lenses Part 1: Complications and Pathology and a Review of Designs," Journal pf Cataract Refractive Surgery, Mar. 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
Cilco Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Egger J.R., "Use of Fresnel Lenses in Optical Systems: Some Advantages and Limitations," in: Atomic and Vlolecular Spectroscopy, vol. 193, Paul R. Yoder, Jr., ed., SPIE Proceedings, the International Society for Optical Engineering, 1979, pp. 63-69.
Einighammer J., et al., "The Individual Virtual Eye: a Computer Model for Advanced Intraocular Lens Calculation, " Journal of optometry, Apr.-Jun. 2009, vol. 2 (2), pp. 70-82.
Farberov, "Manufacturing Fresnel Lenses for Cameras," Soviet Journal of Optical Technology, 1983, vol. 50 (3), pp. 186-188.
Gobin L., et al., "Spherotoric Bag-In-The-Lens Intraocular Lens: Power Calculation and Predictive Misalignment Nomogram, " Journal of Cataract & Refractive Surgery, Jun. 2011, vol. 37 (6), pp. 1020-1030.
Gupta P.A., "Theoretical Analysis of the Fresnel lens As a Function of Design Parameters," Applied Energy, 1981, vol. 9 (4), pp. 301-310.
Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, Feb. 2000, p. 12, 15.

(56) References Cited

OTHER PUBLICATIONS

Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, Dec. 10, 2008, Chap. 3, pp. 27-44.
Monsoriu J.A., et al., "Devil's Lenses," Optics Express, Oct. 17, 2007, vol. 15 (21), pp. 13858-13864.
Naeser K., "Assessment and Statistics of Surgically Induced Astigmatism, " Acta Ophthalmologica, May 2008, vol. 86 Suppl 1, pp. 5-28.
Narvaez J., et al., "Accuracy of Intraocular Lens Power Prediction Using the Hoffer Q, Holladay 1, Holladay 2, and SRK/T formulas, " Journal of Cataract & Refractive Surgery, Dec. 2006, vol. 32 (12), pp. 2050-2053.
Navarro R., et al., "Accommodation-Dependent Model of the Human Eye with Aspherics," Journal of the Optical Society of America, Aug. 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Patel S., et al., "An Evaluation of Unexpected Refractive Outcomes Following Toric IOL Implantation for Astigmatism: A Sector Subtraction Graphical Method for Calculating the Effective Astigmatic Correction, " Research Gate, T.4 No. 2 (6), Jan. 2016, 93 Reads.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modem Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Vanderwerf D., et al., "Approximating the Fresnel Lens," Electro Optical Systems Design, 1982, pp. 47-52.
Vass C., et al., "Prediction of Pseudophakic Capsular bag Diameter based on Biometric Variables," Journal of cataract and Refractive Surgery, Oct. 1999, vol. 25 (10), pp. 1376-1381.
Villegas E.A., et al., "Correlation between Optical and Psychophy, Sical Parameters as a Function of Defocus," Optometry and Vision Science, Jan. 1, 2002, vol. 79 (1), pp. 60-67.

* cited by examiner

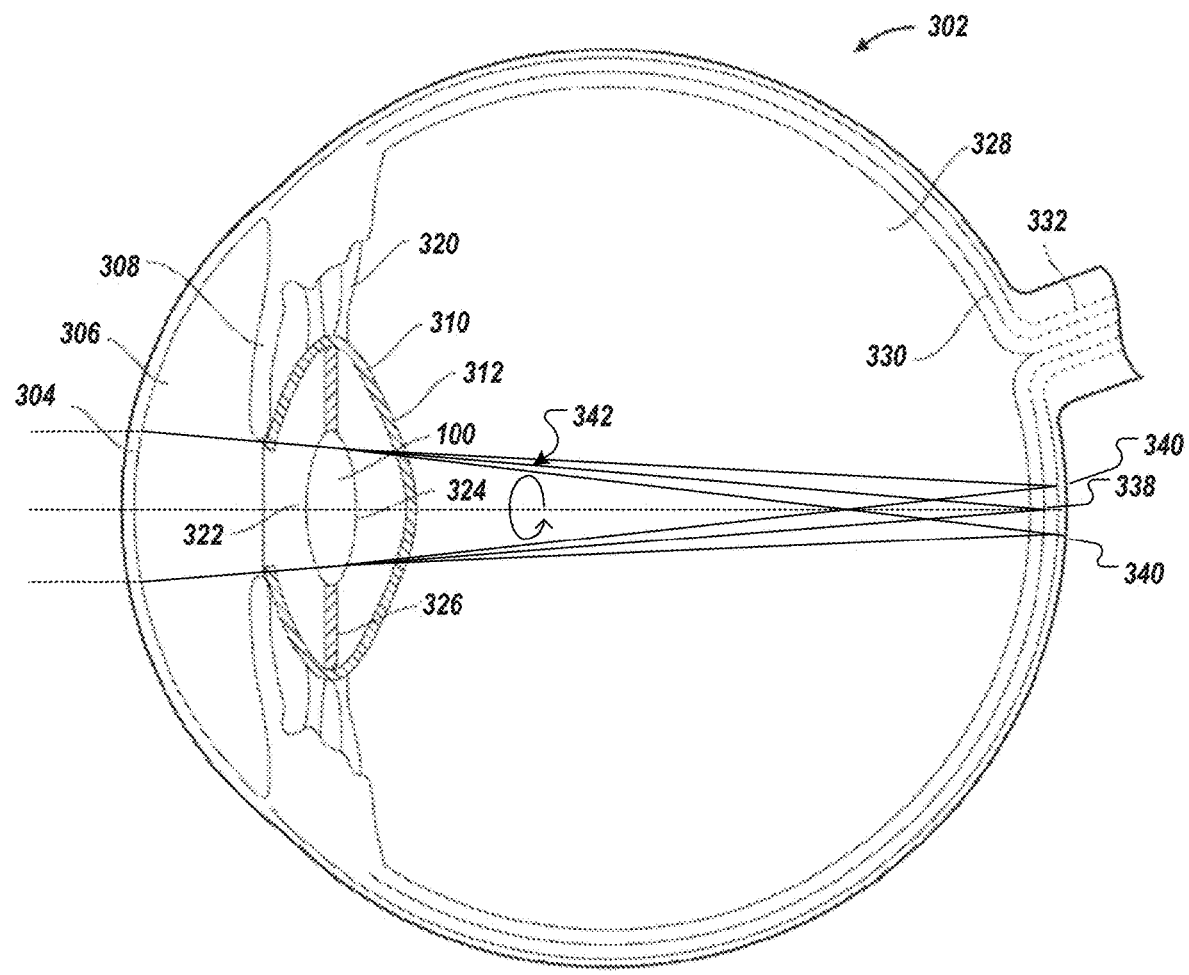
FIG. 3
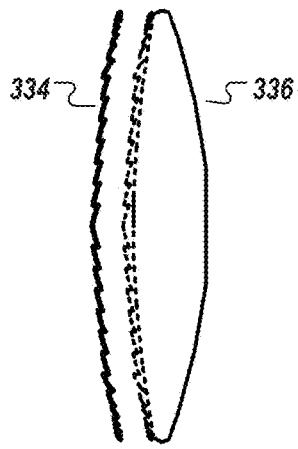
FIG. 4A
FIG. 4B
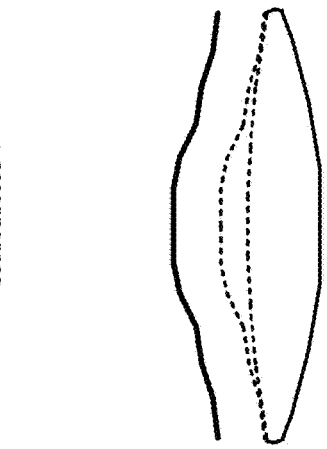
FIG. 4C
FIG. 4D

Tolerance of the misalignment of cylindrical axis

OPHTHALMIC APPARATUS WITH CORRECTIVE MERIDIANS HAVING EXTENDED TOLERANCE BAND WITH FREEFORM REFRACTIVE SURFACES

RELATED APPLICATIONS

This application claims priority to, and the benefit of, U.S. Provisional Appl. No. 62/312,321, filed Mar. 23, 2016, and U.S. Provisional Appl. No. 62/312,338, filed Mar. 23, 2016, each of which is incorporated by reference herein in its entirety.

TECHNICAL FIELD

This application is directed to lenses for correcting astigmatism, including providing increased tolerance for lens placement during implantation.

BACKGROUND

Ophthalmic lenses, such as spectacles, contact lenses and intraocular lenses, may be configured to provide both spherical and cylinder power. The cylinder power of a lens is used to correct the rotational asymmetric aberration of astigmatism of the cornea or eye, since astigmatism cannot be corrected by adjusting the spherical power of the lens alone. Lenses that are configured to correct astigmatism are commonly referred to as toric lenses. As used herein, a toric lens is characterized by a base spherical power (which may be positive, negative, or zero) and a cylinder power that is added to the base spherical power of the lens for correcting astigmatism of the eye.

Toric lenses typically have at least one surface that can be described by an asymmetric toric shape having two different curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting astigmatism of the cornea or eye.

Existing toric lenses are designed to correct astigmatic effects by providing maximum cylindrical power that precisely matches the cylinder axis. Haptics are used to anchor an intraocular lens to maintain the lenses at a desired orientation once implanted in the eye. However, existing toric lenses themselves are not designed to account for misalignment of the lens that may occur during surgical implantation of the lens in the eye or to account for unintended post-surgical movement of the lens in the eye.

One type of toric lens design includes angularly-varying phase members that extend depth of focus features to extend the tolerance band of an intended correction meridian. However, lens design that extends the astigmatism tolerance of a toric IOL are not commonplace.

Accordingly, it would be desirable to have more intraocular lens designs that are tolerant to misalignments.

SUMMARY

The embodiments disclosed herein include improved toric lenses and other ophthalmic apparatuses (including, for example, contact lens, intraocular lenses (IOLs), and the like) and associated method for their design and use. In some embodiments, an ophthalmic apparatus (e.g., toric lens) having regions of one or more base spherical powers and one or more cylinder powers that are added to the one or more base spherical power for correcting an astigmatism (e.g., an intended astigmatism). The apparatus includes one or more optical zones, including a first optical zone defined by a freeform-polynomial surface area (e.g., as area having one or more refractive surfaces) coincident with one or more distinct cylinder powers, wherein light incident to a first region (as an angularly-varying phase member) of the freeform-polynomial surface area, and regions nearby to the first region, is directed to a first point of focus such that the regions nearby to the first region direct light to the first point of focus when the first freeform-polynomial surface area is rotationally offset from the first region, thereby establishing a band of operational meridian for the apparatus to an intended correction meridian, and wherein the freeform-polynomial surface area is defined as a mathematical expression comprising a combination of one or more polynomial expressions (e.g., Chebyshev-based polynomial expression, Zernike-based polynomial expression, etc.) each having a distinct complex orders.

In some embodiments, at least one of the one or more polynomial expression is selected from the group consisting of a Chebyshev polynomial and a Zernike polynomial.

In some embodiments, the freeform-polynomial surface area establishes the band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the freeform-polynomial surface area has a second height profile T(x,y) (e.g., an extra height profile associated with cylinder power) on a first height profile (e.g., a base or conventional height profile such as a typical aspheric profile), the second height profile being defined as:

$$T(x,y) = \Sigma\{c(i,j) * \cos(i * \arccos(t)) * \cos(j * \arccos(t))\}$$

where $c(i,j)$ is a coefficient based on $i$ and $j$, which are each integers (e.g., having a range between 0 and 10), x and y are spatial locations on the freeform-polynomial surface area, and t is a normalized parameter having values between $-1.0$ and $1.0$.

In some embodiments, the freeform-polynomial surface area has the height profile T(x,y) in which i has an order of 0 to at least 6 and j has an order of 0 to at least 6.

In some embodiments (e.g., where the freeform-polynomial surface area spans the entire optical face of the apparatus), the ophthalmic apparatus comprises an optical face (e.g., the portion of the face surface of the ophthalmic apparatus that include corrective optical structures) that includes the one or more optical zones, the optical face having a boundary defined by a first axis of the face and a second axis of the face (e.g., wherein the first axis is orthogonal to the second axis), and wherein each of the x-spatial locations at value $-1.0$ and at value $1.0$ coincides with, or near, the boundary, and each of the y-spatial locations at value $-1.0$ and at value $1.0$ coincides with, or near, the boundary.

In some embodiments, (e.g., where the freeform-polynomial surface area symmetrically spans part of the optical face of the apparatus), wherein the ophthalmic apparatus comprises an optical face (e.g., the portion of the face surface of the ophthalmic apparatus that include corrective optical structures) that includes the one or more optical zones, the optical face having a boundary defined by a first axis of the face and a second axis of the face (e.g., wherein the first axis is orthogonal to the second axis), and wherein each of the x-spatial locations at value −1.0 and at value 1.0 is located at a first radial position along the first axis between a center location of the ophthalmic apparatus and the boundary, and wherein each of the y-spatial locations at value −1.0 and at value 1.0 is located at the first radial position along the second axis between a center location of the ophthalmic apparatus and the boundary.

In some embodiments, the freeform-polynomial surface area has for each continuously distributed contour line at the IOL plane a difference of less than about 0.6 Diopters.

In some embodiments (e.g., for a multiple zonal structure), the one or more optical zones includes a second optical zone defined by a second freeform-polynomial surface region, wherein the second freeform-polynomial surface area is characterized and defined by a second polynomial.

In some embodiments, the second freeform polynomial surface area has a second height profile that varies according to a freeform polynomial selected from the group consisting of a Chebyshev polynomial and a Zernike polynomial.

In some embodiments (e.g., for a multiple zonal structure), the one or more optical zones includes a second optical zone defined by a second freeform-polynomial surface region, wherein the second freeform-polynomial surface area is characterized and defined by a second combination of one or more polynomial expressions (e.g., Chebyshev-based polynomial expression, Zernike-based polynomial expression, etc.) each having a distinct complex orders.

In some embodiments, at least one of the one or more polynomial expression is selected from the group consisting of a Chebyshev polynomial and a Zernike polynomial.

In some embodiments (e.g., for a multiple zonal structure where the second freeform-polynomial surface area provides a second correction), the second freeform-polynomial surface area is configured to direct light incident to a second region of the second freeform-polynomial surface area, and regions nearby to the second region to a second point of focus such that the regions nearby to the second region direct light to the second point of focus when the second freeform-polynomial surface area is rotationally offset from the second region.

In some embodiments (e.g., for a multiple zonal structure where the second freeform-polynomial surface area adds to the correction power of the first freeform-polynomial surface), the second freeform-polynomial surface area is configured to direct light incident to a second region of the second freeform-polynomial surface area, and regions nearby to the second region, to the first point of focus such that the regions nearby to the second region direct light to the first point of focus when the second freeform-polynomial surface area is rotationally offset from the second region (e.g., over the band of operational meridian).

In some embodiments, the second freeform-polynomial surface area has a third height profile $T_2(x,y)$ (e.g., associated with cylinder power) on a first height profile (e.g., a base or conventional height profile such as a typical aspheric profile), the third height profile being defined as:

$$T_2(x,y)=\Sigma\{c_2(i_2,j_2)*\cos(i_2*\arccos(t_2))*\cos(j_2*\arccos(t_2))\}$$

where $c_2(i_2,j_2)$ is a coefficient based on $i_2$ and $j_2$, which are each integers (e.g., ranging between 0 and 10), x and y are spatial locations on the second freeform-polynomial surface area and $t_2$ has values between −1.0 and 1.0.

In some embodiments, the first freeform-polynomial surface area comprise a monofocal lens, a bifocal lens, or a multi-focal lens.

In some embodiments, the second freeform-polynomial surface area comprise a monofocal lens, a bifocal lens, or a multi-focal lens.

In some embodiments, the first freeform-polynomial surface area comprise an extended range of vision lens.

In some embodiments, the second freeform-polynomial surface area comprise an extended range of vision lens.

In some embodiments, the first freeform-polynomial surface area comprises refractive surfaces.

In some embodiments, the first freeform-polynomial surface area comprises diffractive surfaces.

In another aspect, a method is disclosed of designing an ophthalmic apparatus having regions of one or more base spherical powers and one or more cylinder powers that are added to the one or more base spherical power for correcting an astigmatism (e.g., an intended astigmatism). The method includes generating, via a processor, one or more optical zones, including a first optical zone defined by a freeform-polynomial surface area (e.g., as area having one or more refractive surfaces) coincident with one or more distinct cylinder powers, wherein light incident to a first region of the freeform-polynomial surface area, and regions nearby to the first region, is directed to a first point of focus such that the regions nearby to the first region direct light to the first point of focus when the first freeform-polynomial surface area is rotationally offset from the first region, thereby establishing a band of operational meridian for the apparatus to an intended correction meridian, and wherein the freeform-polynomial surface area is defined as a mathematical expression comprising a combination of one or more polynomial expressions (e.g., Chebyshev-based polynomial expression, Zernike-based polynomial expression, etc.) each having a distinct complex orders.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 3 is a schematic drawing of a top view of a human eye, in which the natural lens of the eye has been removed and replaced with an ophthalmic apparatus that includes an exemplified freeform-polynomial surface area, in accordance with an illustrative embodiment.

FIGS. 4A, 4B, 4C, and 4D are schematic diagrams of exemplary ophthalmic apparatuses that include either refractive or diffractive freeform-polynomial surfaces, in accordance with an illustrative embodiment.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present disclosure find particular use in or on the eyes of human or animal subjects. Embodiments of the present disclosure are illustrated below with particular reference to intraocular lenses; however, other types of lenses fall within the scope of the present disclosure. Embodiments of the present disclosure provide improved ophthalmic lens (including, for example, contact lenses, and intraocular lenses, corneal lenses and the like) and include monofocal refractive lenses, monofocal diffractive lenses, bifocal refractive lenses, bifocal diffractive lenses, and multifocal refractive lenses, multifocal diffractive lenses.

As used herein, the term "refractive optical power" or "refractive power" means optical power produced by the refraction of light as it interacts with a surface, lens, or optic. As used herein, the term "diffractive optical power" or "diffractive power" means optical power resulting from the diffraction of light as it interacts with a surface, lens, or optic.

As used herein, the term "optical power" means the ability of a lens or optics, or portion thereof, to converge or diverge light to provide a focus (real or virtual), and is commonly specified in units of reciprocal meters (m−1) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. Except where noted otherwise, the optical power of a lens or optic is from a reference plane associated with the lens or optic (e.g., a principal plane of an optic). As used herein, a cylinder power refers to the power required to correct for astigmatism resulting from imperfections of the cornea and/or surgically induced astigmatism.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Figure 1:
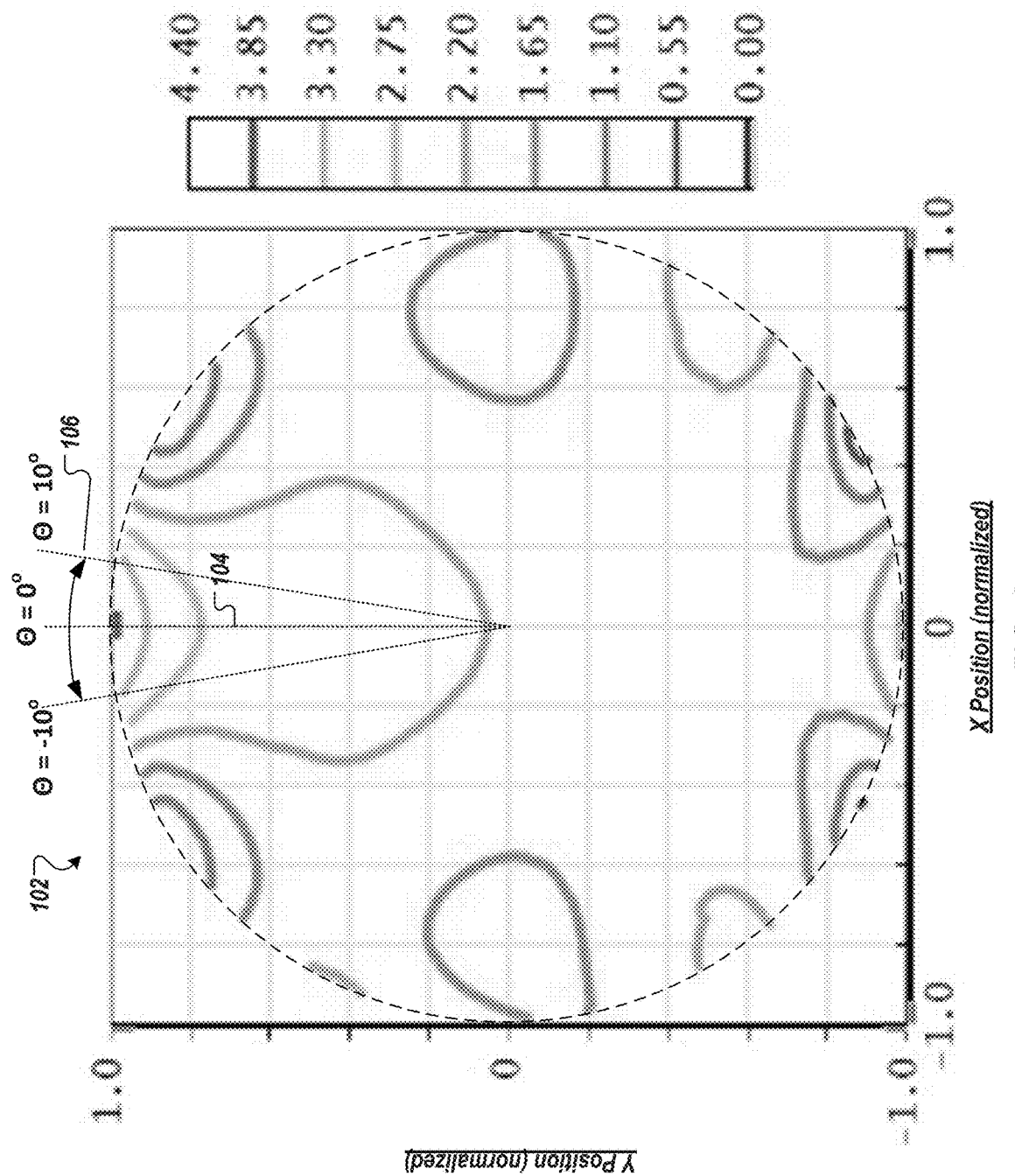
FIG. 1 is a diagram of a freeform-polynomial surface area that provides extended rotational tolerance, in accordance with an illustrative embodiment.

FIG. 1 is a diagram of an example freeform-polynomial surface area 102 that provides extended rotational tolerance, in accordance with an illustrative embodiment. The freeform-polynomial surface area 102 is mapped to a surface of an ophthalmic apparatus 100 (not shown—see FIG. 3) to provide cylinder power to the ophthalmic apparatus, e.g., for the correction an astigmatism, or the like, such that the ophthalmic apparatus can be subjected to a cylindrical axis misalignment (CAM) (shown via arrow 106) of the meridian 104 (also referred to as "axis' 104) of up to 10 degrees without degradation of the corrective performance (e.g., with regard to visual acuity (VA) or modular transfer function (MTF)), as compared to when there no misalignment.

Notably, the freeform-polynomial surface area 102 is defined as a mathematical expression that is a combination of one or more polynomial expressions each having a distinct complex orders. Examples of polynomial expressions includes, but are not limited to, Chebyshev-based polynomial expression, Zernike-based polynomial expression. The combination of one or more polynomial expressions may be used to define an angularly-varying phase member that is tolerant of cylindrical axis misalignment (CAM) up to an extended band of operation without degradation of the corrective performance such as visual acuity (VA) or modular transfer function (MTF) as compared to when there no misalignment.

In some embodiments, one or more polynomial expressions are combined with different complex orders and the results are tested to determine that corrective performance (e.g., with regard to visual acuity (VA) or modular transfer function (MTF) are met.

As used herein, a "Chebyshev-based polynomial" refers to a mathematical expression that is expressed as a combination of one or more Chebyshev polynomial components in which the Chebyshev polynomial components is a Chebyshev polynomials of the first kind and/or a Chebyshev polynomials of the second kind. The Chebyshev polynomial can include, as a combination, the Chebyshev polynomial component along with another polynomial expression (e.g., Zernike polynomials, combinations of Zernike polynomials, other polynomials, or combination thereof, and etc.)

As used herein, a "Zernike-based polynomial" refers to a mathematical expression that is expressed as a combination of one or more Zernike polynomial components in which the Zernike polynomial components is a Zernike polynomial. The Zernike polynomial can include, as a combination, a Zernike polynomial component along with another polynomial expression (e.g., Chebyshev polynomials, combinations of Chebyshev polynomials, other polynomials, or combination thereof, and etc.)

Referring back to FIG. 1, the freeform-polynomial surface area 102 of FIG. 1 is defined as a mathematical expression that is a combination of one or more polynomial expressions each having a distinct complex orders. In some embodiments, the freeform-polynomial surface area 102 is defined as a second thickness value T(x,y) for a cylinder surface superimposed on a first thickness value (e.g., a base or typical aspheric height profile), in which T(x,y) is defined by Equation 1:

$$T(x,y)=\Sigma\{c(i,j)*\cos(i*\arccos(t))*\cos(j*\arccos(t))\} \quad \text{(Equation 1)}$$

where c(i,j) is a coefficient based on i and j, which are each orders of the polynomial and expressed as integers, x and y are spatial locations on the freeform-polynomial surface area, and t is a normalized parameter for angular positions having values between −1.0 and 1.0. The base thickness value can be from a typical aspheric thickness profile. In some embodiments, the coefficient c(i,j) is based on a basis function that adjust the normalized amplitudes of each respective location of the lens as represented by the Chebyshev polynomial. A Chebyshev polynomial (of the first kind), along one dimension, can be expressed as $T_k(x)=\cos(k*\cos^{-1}(x))$, where k is an order that is an integer. In two dimension, a Chebyshev polynomial (of the first kind) can be expressed as $T_{ij}(x,y)=\text{COS}(i*\cos^{-1}(x))*\text{COS}(j*\cos^{-1}(y))$, where x and y values have a numerical value between −1.0 and +1.0, and $T_{ij}$ are normalized to a value of −1.0 and +1.0.

Referring still to FIG. 1, the freeform-polynomial surface area 102 of FIG. 1 is derived from Chebyshev polynomials as shown in Equation 1 having i-order of 0 to 6 and a j-order of 0 to 6. Equation 2 shows the expanded mathematical expression for the second freeform-polynomial surface area 102 of FIG. 1.

$$\begin{aligned}T(x, y) = &\ c(0, 0)^*\cos(0^*\cos^{-1}(t))^*\cos(0^*\cos^{-1}(t)) + \\ &\ c(0, 1)^*\cos(0^*\cos^{-1}(t))^*\cos(1^*\cos^{-1}(t)) + \\ &\ c(0, 2)^*\cos(0^*\cos^{-1}(t))^*\cos(2^*\cos^{-1}(t)) + \\ &\ c(0, 3)^*\cos(0^*\cos^{-1}(t))^*\cos(3^*\cos^{-1}(t)) + \\ &\ c(0, 4)^*\cos(0^*\cos^{-1}(t))^*\cos(4^*\cos^{-1}(t)) + \\ &\ c(0, 5)^*\cos(0^*\cos^{-1}(t))^*\cos(5^*\cos^{-1}(t)) + \\ &\ c(0, 6)^*\cos(0^*\cos^{-1}(t))^*\cos(6^*\cos^{-1}(t)) + \\ &\ c(1, 0)^*\cos(1^*\cos^{-1}(t))^*\cos(0^*\cos^{-1}(t)) + \\ &\ c(1, 1)^*\cos(1^*\cos^{-1}(t))^*\cos(1^*\cos^{-1}(t)) + \\ &\ c(1, 2)^*\cos(1^*\cos^{-1}(t))^*\cos(2^*\cos^{-1}(t)) + \\ &\ c(1, 3)^*\cos(1^*\cos^{-1}(t))^*\cos(3^*\cos^{-1}(t)) + \\ &\ c(1, 4)^*\cos(1^*\cos^{-1}(t))^*\cos(4^*\cos^{-1}(t)) + \\ &\ c(1, 5)^*\cos(1^*\cos^{-1}(t))^*\cos(5^*\cos^{-1}(t)) + \\ &\ c(1, 6)^*\cos(1^*\cos^{-1}(t))^*\cos(6^*\cos^{-1}(t)) + \\ &\ \ldots c(6, 0)^*\cos(6^*\cos^{-1}(t))^*\cos(0^*\cos^{-1}(t)) + \\ &\ c(6, 1)^*\cos(6^*\cos^{-1}(t))^*\cos(1^*\cos^{-1}(t)) + \\ &\ c(6, 2)^*\cos(6^*\cos^{-1}(t))^*\cos(2^*\cos^{-1}(t)) + \\ &\ c(6, 3)^*\cos(6^*\cos^{-1}(t))^*\cos(3^*\cos^{-1}(t)) + \\ &\ c(6, 4)^*\cos(6^*\cos^{-1}(t))^*\cos(4^*\cos^{-1}(t)) + \\ &\ c(6, 5)^*\cos(6^*\cos^{-1}(t))^*\cos(5^*\cos^{-1}(t)) + \\ &\ c(6, 6)^*\cos(6^*\cos^{-1}(t))^*\cos(6^*\cos^{-1}(t)) = \\ &\ c(0, 0) + c(0, 1)^*\cos(\cos^{-1}(t)) + \\ &\ c(0, 2)^*\cos(\cos(2^*\cos^{-1}(t)) + c(0, 3)^*\cos(3^*\cos^{-1}(t)) + \\ &\ c(0, 4)^*\cos(4^*\cos^{-1}(t)) + c(0, 5)^*\cos(5^*\cos^{-1}(t)) + \\ &\ c(0, 6)^*\cos(6^*\cos^{-1}(t)) + c(1, 0)^*\cos(\cos^{-1}(t)) + \\ &\ c(1, 1)^*\cos(\cos^{-1}(t))^*\cos(\cos^{-1}(t)) + \\ &\ c(1, 2)^*\cos(\cos^{-1}(t))^*\cos(2^*\cos^{-1}(t)) + \\ &\ c(1, 3)^*\cos(\cos^{-1}(t))^*\cos(3^*\cos^{-1}(t)) + \\ &\ c(1, 4)^*\cos(\cos^{-1}(t))^*\cos(4^*\cos^{-1}(t)) + \\ &\ c(1, 5)^*\cos(\cos^{-1}(t))^*\cos(5^*\cos^{-1}(t)) + \\ &\ c(1, 6)^*\cos(\cos^{-1}(t))^*\cos(6^*\cos^{-1}(t)) + \\ &\ \ldots c(6, 0)^*\cos(6^*\cos^{-1}(t))^*\cos(0^*\cos^{-1}(t)) + \\ &\ c(6, 1)^*\cos(6^*\cos^{-1}(t))^*\cos(1^*\cos^{-1}(t)) + \\ &\ c(6, 2)^*\cos(6^*\cos^{-1}(t))^*\cos(2^*\cos^{-1}(t)) + \\ &\ c(6, 3)^*\cos(6^*\cos^{-1}(t))^*\cos(3^*\cos^{-1}(t)) + \\ &\ c(6, 4)^*\cos(6^*\cos^{-1}(t))^*\cos(4^*\cos^{-1}(t)) + \\ &\ c(6, 5)^*\cos(6^*\cos^{-1}(t))^*\cos(5^*\cos^{-1}(t)) + \\ &\ c(6, 6)^*\cos(6^*\cos^{-1}(t))^*\cos(6^*\cos^{-1}(t))\end{aligned} \quad \text{(Equation 2)}$$

Referring still to FIG. 1, a power pupil map with uniformly distributed contour lines of the calculated cylindrical power for the freeform-polynomial surface area 102 is shown. The corrective meridian is located at about Θ=0° (shown as axis 104) with a center portion of the freeform-polynomial surface area 102 being disposed at this Θ position. Off-center structures of the freeform-polynomial surface area 102 extend from the center structure in a gradually varying manner (e.g., as defined by the combination of Chebyshev polynomials described in relation to Equation 2) to apply cylinder power to a band of meridians surrounding the corrective meridian enabling the ophthalmic apparatus to operate off-axis (or off-meridian) to the corrective meridian (e.g., the astigmatism meridian). Notably, there are no more than 0.6-Diopter difference between any neighboring uniformly distributed contour lines.

Figure 2:
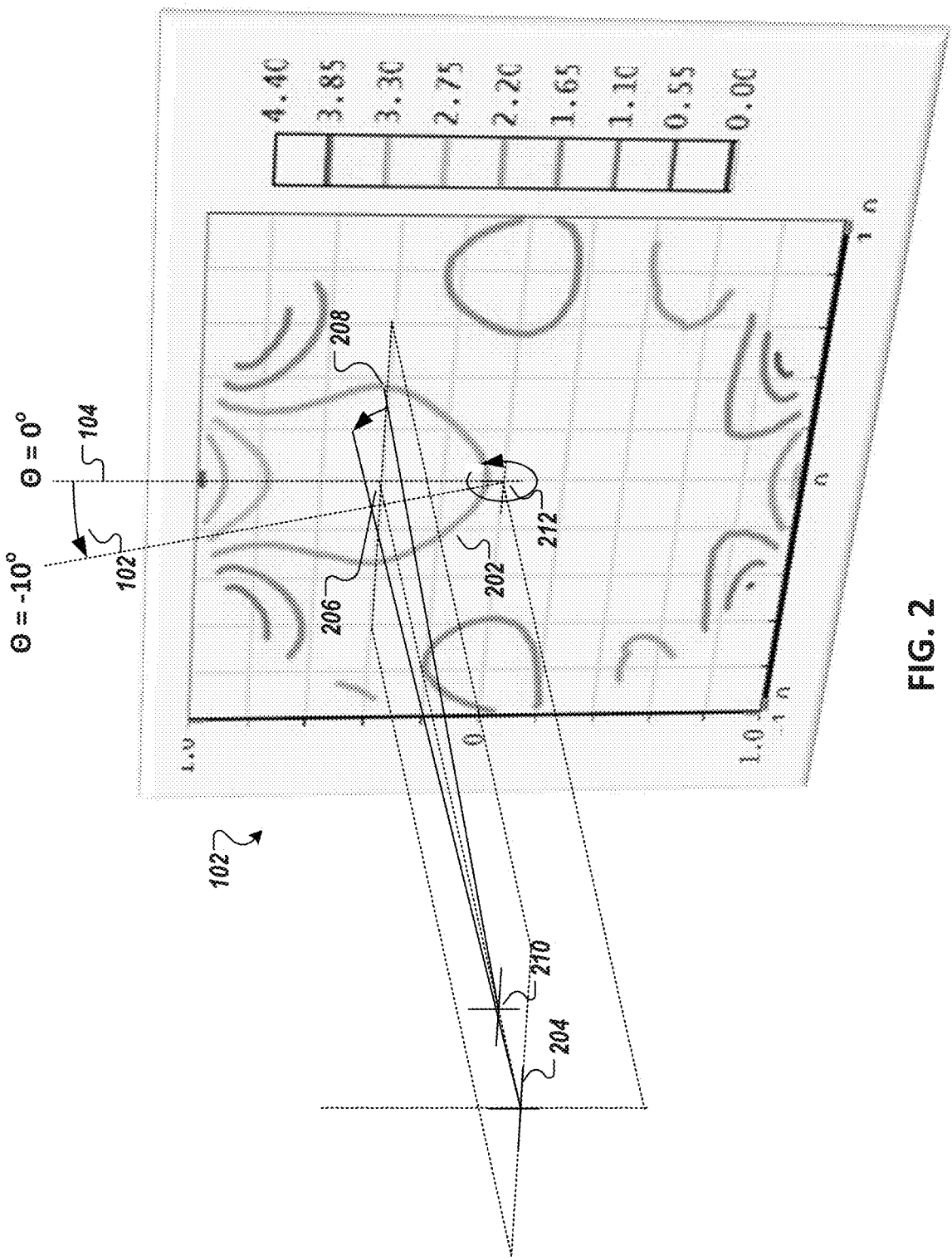
FIG. 2 illustrates an example operation of the freeform-polynomial surface area of FIG. 1 when subjected to misalignment, in accordance with an illustrative embodiment.

FIG. 2 illustrates an example operation of the freeform-polynomial surface area of FIG. 1 when subjected to misalignment, in accordance with an illustrative embodiment. The freeform-polynomial surface area 102, as a diffractive or refractive structure, in some embodiments, varies the extended depth of focus to a plurality of nearby focus points. To this end, light directed to such nearby focus points are thus directed to the desired focus point when the ophthalmic apparatus is subjected to a rotational offset from a primary intended axis of alignment, thereby extending the rotational tolerance of the apparatus to an extended tolerance band. In FIG. 2, a portion (202) of the freeform-polynomial surface area 102 has a focus point 204 (e.g., referred to as a "main focus point" 204, e.g., to correct for an astigmatism) that is generated by a region about the center 206 of the portion 202 of the freeform-polynomial surface area 102. In this example, a nearby region 208 of that portion 202 has a focus point 210 (e.g., referred to as an "auxiliary focus point" 210) that is offset from the main focus point 204. When the freeform-polynomial surface area 102 is rotated about axis 212, e.g., as misalignment 102 is introduced to the corrective meridian Θ=0° (104), the focus point 210 of region 208 is moved towards the main focus point 204, thereby extending the band of operation of the freeform-polynomial surface area 102. Remarkably, this extended tolerance astigmatism band delivers cylinder power to correct for the astigmatism for a range of meridians (e.g., up to ±10° as shown in FIG. 1, though can be more in other embodiments), thereby eliminating any need for additional corrective measures (e.g., supplemental corrective devices or another surgical intervention) when the implanted ophthalmic apparatus is not perfectly aligned to the desired astigmatism meridian in the eye.

Put another way, the freeform-polynomial surface area 102 facilitates an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

Corneal Irregular Geometry or Limited Retinal Area Functions

In another aspect, the freeform-polynomial surface area 102 of FIG. 1 is optimized to purposely place accumulated high surface amplitude to non-functional retinal area so that the functional areas can fully benefit the enhanced image quality stability of the freeform-polynomial surface design. Examples of non-functional retinal areas may include, but not limited to, areas of gradual loss of sight (e.g., associated with glaucoma or retinal macular degeneration (e.g., age-related macular degeneration, AMD). The freeform-polynomial surface area 102 of FIG. 1 can be similarly optimized to emphasize needs for a cornea that irregularly shaped with or without astigmatism and with local Keratoconus with or without astigmatism.

In particular, the freeform-polynomial surface area 102, in some embodiments, are optimized by further modification of the weights (e.g., c(i,j) as discussed in relation to Equation 1 or Equation 2) in the combined Chebyshev polynomials and the Zernike or extended polynomials used to characterize or design the geometry of the freeform-polynomial surface area 102. As noted above, the c(i,j) is used to scale the normalized surface generated by the Chebyshev polynomials or the Zernike polynomials. C(i,j) is also used to adjust and/or emphasize cylindrical power for corneal irregular geometry or limited retinal area functions.

As shown in Equations 1 and 2, the freeform-polynomial surface area 102 is defined by a surface sag (or power) that is a weighted sum of Chebyshev polynomials (Zernike and other polynomials may be used with, or in substitute of, the Chebyshev polynomials) with the coefficient c(i,j) (e.g., shown in Equation 1).

The coefficient c(i,j) are weights that may be modified or set based on specific knowledge of the local coordinates of the special cornea irregularity. To this end, the coefficient c(i,j) allows the specific polynomials to be freely shifted in space (i.e., spatial) domain to match the local coordinates. The coefficient c(i,j) as weights for each polynomial can be a function of local coordinates function and implemented as a filter with low-, medium-, or high-pass transmission operations.

Example Operation of Exemplified Freeform-Polynomial Surfaces

FIG. 3 is a schematic drawing of a top view of a human eye 302, in which the natural lens of the eye 302 has been removed and replaced with an intraocular lens 100 (shown in simplified form in FIG. 3 and in greater detail in FIGS. 4A, 4B, 4C, and 4D). Light enters from the left of FIG. 3, and passes through the cornea 304, the anterior chamber 306, the iris 308, and enters the capsular bag 310. Prior to surgery, the natural lens occupies essentially the entire interior of the capsular bag 310. After surgery, the capsular bag 310 houses the intraocular lens 100, in addition to a fluid that occupies the remaining volume and equalizes the pressure in the eye.

After passing through the intraocular lens, light exits the posterior wall 312 of the capsular bag 310, passes through the posterior chamber 328, and strikes the retina 330, which detects the light and converts it to a signal transmitted through the optic nerve 332 to the brain. The intraocular lens 100 comprises an optic 324 and may include one or more haptics 326 that are attached to the optic 324 and may serve to center the optic 324 in the eye and/or couple the optic 324 to the capsular bag 310 and/or zonular fibers 320 of the eye.

The optic 324 has an anterior surface 334 and a posterior surface 336, each having a particular shape that contributes to the refractive or diffractive properties of the lens. Either or both of these lens surfaces may optionally have an element made integral with or attached to the surfaces. FIGS. 4A, 4B, 4C, and 4D are schematic diagrams of exemplary ophthalmic apparatuses that include the freeform-polynomial surface area 102, in accordance with an illustrative embodiment. Specifically, FIGS. 4A and 4B show examples of diffractive lenses, and FIGS. 4C and 4D show examples of refractive lenses.

Referring still to FIG. 3, the intraocular lens 100 includes freeform-polynomial surface area 102 (as a refractive, diffractive, or both) that focus at a plurality of focus points that are offset radially to one another so as to provide an extended tolerance to misalignments of the lens 100 when implanted into the eye 302. That is, when the center axis of a corrective meridian is exactly matched to the desired astigmatic axis, only a first portion of the cylinder axis is focused at the desired point of focus (338) (e.g., at the retina) while second portions of the cylinder axis focuses at other points (340) nearby that are radially offset to the desired point of focus (338). To this end, when the primary axis of the astigmatism of the intraocular lens is rotationally offset (shown as arrow 342) with the astigmatism of the eye, the second portion of the cylinder axis focuses the light to the desired point of focus.

Artificial lenses (e.g., contact lenses or artificial intraocular lenses) can correct for certain visual impairments such as an inability of the natural lens to focus at near, intermediate or far distances; and/or astigmatism. Intraocular toric lenses have the potential for correcting astigmatism while also correcting for other vision impairments such as cataract, presbyopia, etc. However, in some patients, implanted intraocular toric lenses may not adequately correct astigmatism due to rotational misalignment of the corrective meridian of the lenses with the astigmatic meridian. In some patients following the surgical implant of the toric lenses, the corrective meridian of the implanted toric lenses can be rotationally misaligned to the astigmatic meridian, in some instances, by as much as 10 degrees. However, toric lenses that are designed to provide maximum correction (e.g., 1 D to 9 D) at the astigmatic meridian are subject to significant reduction in effectiveness of the correction due to any misalignment from the corrective meridian. In certain designs, it is observed that if the cylindrical power axis were mismatched by 1 degree, there would be about 3 percent reduction of the effectiveness of the correction. The degradation increases with the degree of misalignment. If there were a 10-degree misalignment, there would be about 35% reduction of the effectiveness of the correction. This effect is illustrated in FIG. 5 discussed below.

Figure 5:
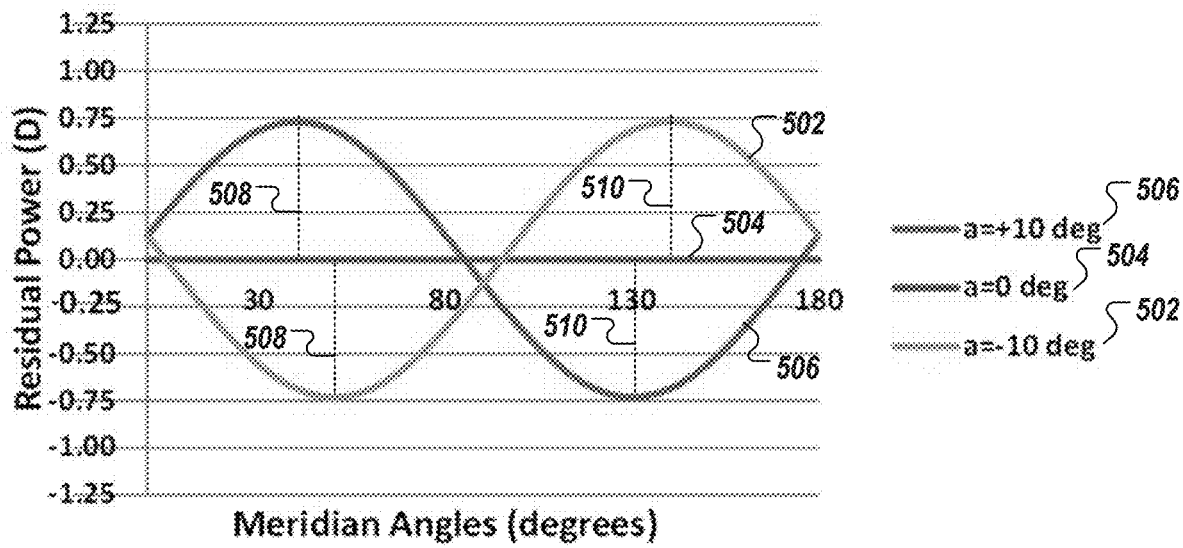
FIGS. 5 and 6 include plots that illustrated the degraded performance of conventional toric lens when subjected to rotational misalignments.
Figure 6:
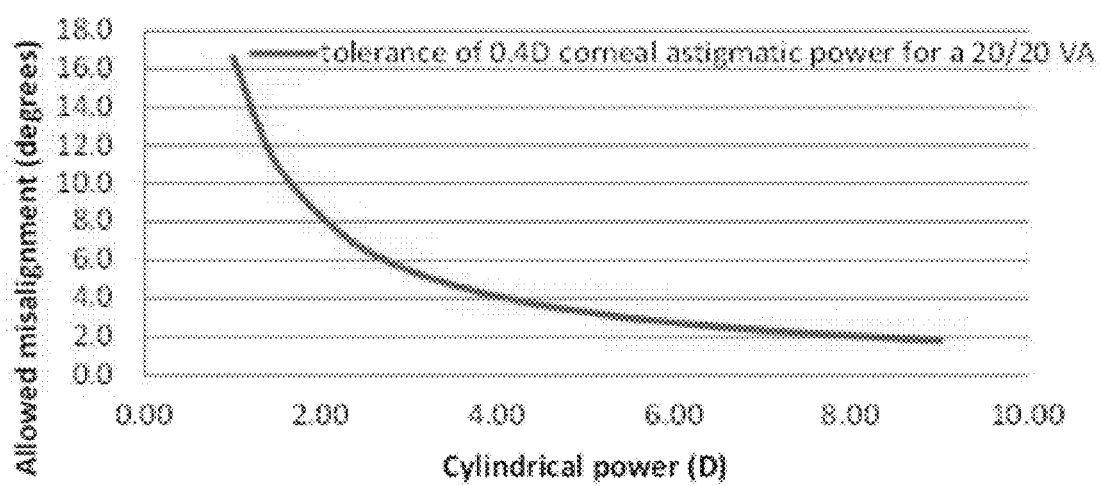

FIGS. 5 and 6 include plots that illustrated the above-discussed degraded performance of conventional toric lens when subjected to rotational misalignments. This conventional toric lens is configured to provide 6.00 Diopters cylinder powers at the IOL plane, 4.11 Diopters cylinder power at the corneal plane, and a corneal astigmatism correction range (i.e., preoperative corneal astigmatism to predicted effects) between 4.00 and 4.75 Diopters.

Referring to FIG. 5, a plot of the undesired meridian power (also referred to as a residual meridian power ("OC")) (shown along the y-axis) added due to the rotational misalignments (shown along the x-axis) of the toric IOL is shown, including the residual powers for i) a negative 10-degree misalignment (shown as line 502), ii) a 0-degree misalignment (shown as line 504), and iii) a positive 10-degree misalignment (shown as line 506). As shown, the undesired added meridian power varies between a maximum of ±0.75 Diopters at around the 45-degree meridian angle (shown as 508) and at about the 135-degree meridian angle (shown as 510). Notably, this undesired added meridian power is outside the tolerance of a healthy human eye, which can tolerant undesired effects up to about 0.4 Diopters (e.g., at the cornea plane) for normal visual acuity (i.e., "20/20 vision"). Because the undesired effects exceeds the astigmatism tolerance of the human eye, corrective prescription glasses, or further surgical operation to correct the implant misalignment, may be necessary to mitigate the effects of the misalignment of such toric IOLs.

This undesired meridian power, conventionally, may be expressed as Equation 1 below.

$$OC = 2\sin\alpha * \frac{C}{2} 0.7\cos\left(2\left(\theta + 90 + \frac{\alpha}{2}\right)\right) \quad \text{(Equation 3)}$$

As shown in Equation 3, θ is the correction meridian (also referred to as the cylindrical power axis) (in degrees); C is the astigmatic power (at the IOL plane) to be corrected at meridian θ (in Diopters); and a is the magnitude of rotational misalignment of the cylindrical power axis to the astigmatic axis (in degrees).

FIG. 6 shows a plot illustrating the tolerance of a toric IOL to misalignment (shown in the y-axis) and a corresponding cylindrical power that may be applied (shown in the x-axis) for each misalignment to not exceed the astigmatism tolerance of the human eye (i.e., degrade the overall visual acuity). The tolerance to misalignment may be calculated as $$|\alpha| \leq \sin^{-1} \frac{\frac{0.4}{2}}{\frac{C}{0.7}}$$

where α is the magnitude of rotational misalignment (in degrees). The calculation may be reduced to $$|\alpha| \leq \sin^{-1} \frac{0.29}{C}.$$

As shown, for a misalignment of 5 degrees, which is routinely observed in IOL implantations, the correction effectiveness of such IOL implants can only be maintained for a toric IOL with 3.75 Diopters or less. That is, a toric IOL having cylinder power above 3.75 Diopters would exhibit degraded visual acuity due to the residual power exceeding the astigmatism tolerance of a human eye. This effect worsens with further degrees of misalignment. For example, at about 10 degrees, the effectiveness of a toric IOL is greatly reduced where only 1.5 Diopters cylinder power or less can be applied so as to not detrimentally affect the visual acuity. Given that cylinder power of convention toric IOLs may range between 1.00 Diopters and 9.00 Diopters, these toric IOLs are reduced in effectiveness post-operation due to the misalignments of cylinder axis.

Results of IOL with Exemplified Freeform-Polynomial Surfaces

Figure 7:
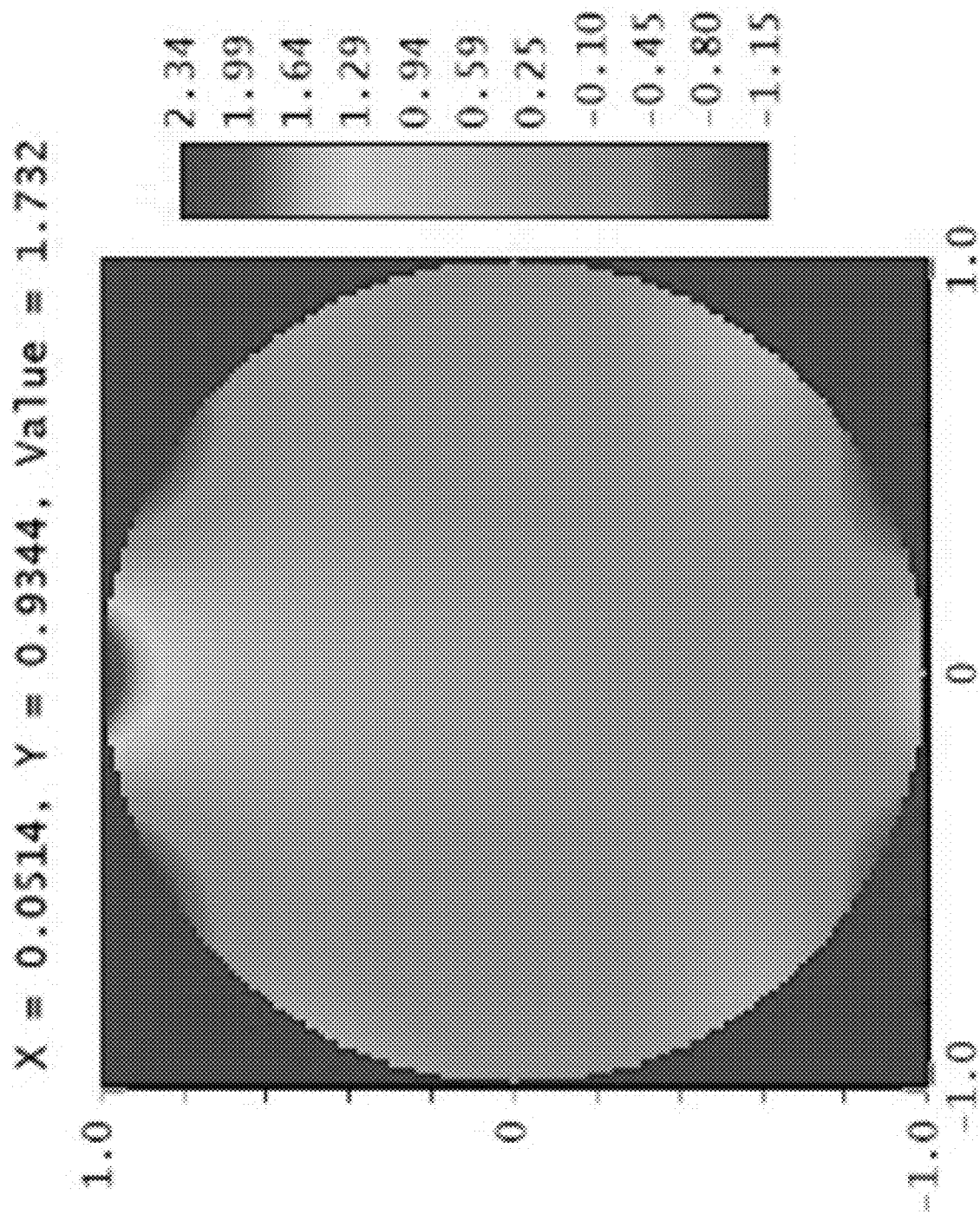
FIG. 7 shows a combined cylinder map generated from the combination of the IOL cylindrical power (provided, in part, via the freeform-polynomial surface of FIG. 1) combined with the an example corneal cylindrical power through meridians.

FIG. 7 shows a combined cylinder map generated from the combination of the IOL cylindrical power (provided, in part, via the freeform-polynomial surface) combined with the corneal cylindrical power through meridians. As discussed above with reference to FIG. 1, and as can be seen from the IOL cylinder map through meridians around the clock, there is remarkably no more than about 0.6 D difference for any continuous uniformly distributed contour lines at the IOL plane. The IOL SE is 20 D at the IOL plane. The IOL cylinder map of FIG. 1 is combined with the IOL SE to provide the overall IOL cylindrical map. This overall IOL cylindrical map is then combined with a test corneal cylindrical power. The resulting combination (shown in FIG. 7) remarkably shows little variation in the cylinder map of the combined IOL cylindrical power the corneal cylindrical power. That is, the astigmatism associated with test corneal cylindrical power has been attenuated and/or corrected for by the IOL cylindrical power provided, in part, by the freeform-polynomial surface.

Figure 8A:
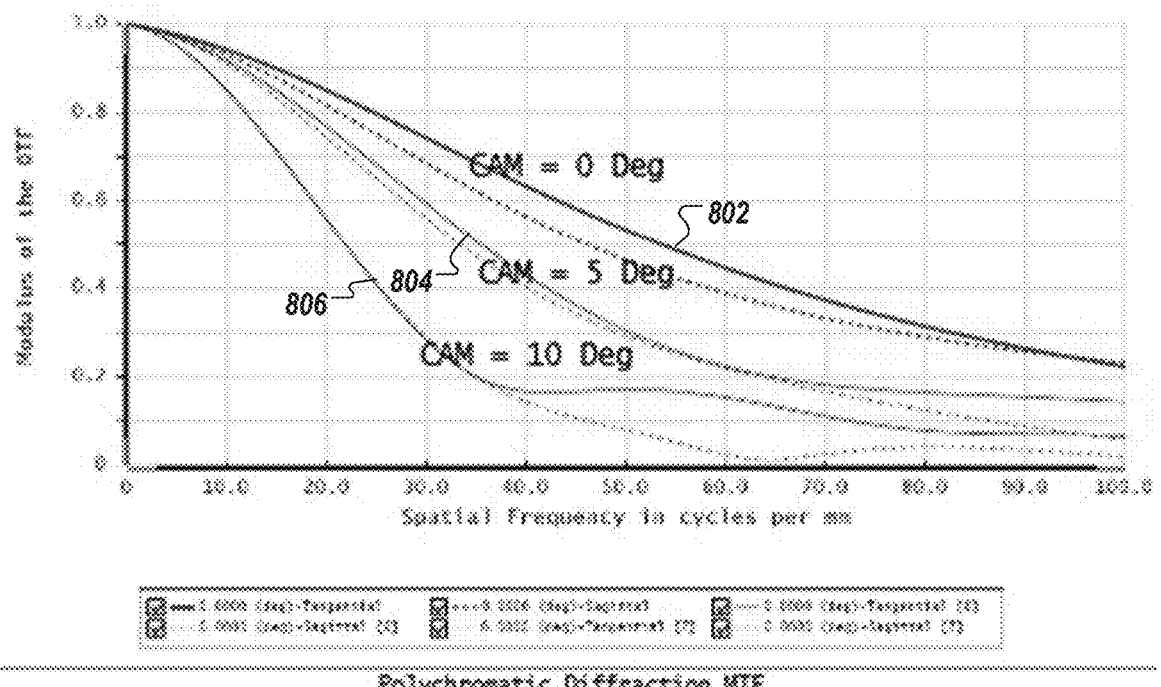
FIGS. 8A and 8B each shows calculated MTF values as spatial frequencies of an exemplified IOL in a physiological eye model with astigmatic cornea in different cylindrical axis misalignment (CAM) situations between the cornea and the IOL for an iris pupil.
Figure 8B:
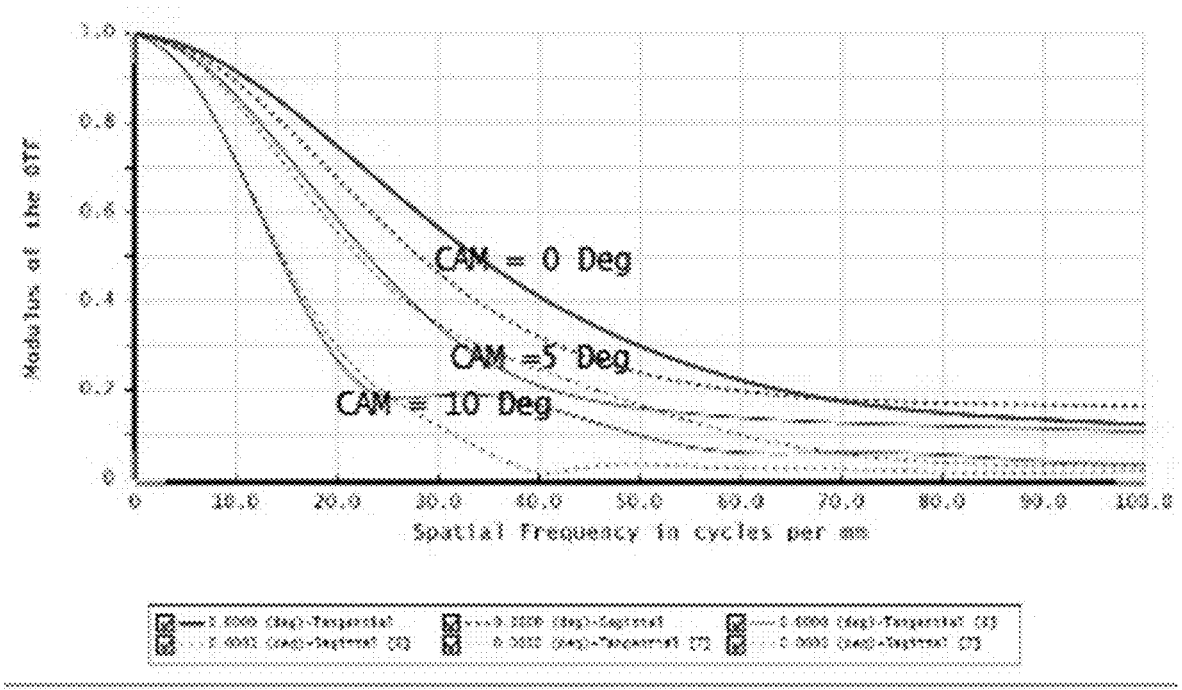

FIGS. 8A and 8B each shows calculated MTF values as spatial frequencies of an exemplified IOL 100 in a physiological eye model with astigmatic cornea in different cylindrical axis misalignment (CAM) situations between the cornea and the IOL for an iris pupil. Notably, as shown in FIGS. 8A and 8B, the modulation transfer function (MTF) is maintained across the extended range of alignment for a lens configured with the freeform-polynomial surface area 102 of FIG. 1. Specifically, in FIGS. 8A and 8B, the MTFs for misalignment at 0 degrees, 5 degrees, and 10 degrees are shown (shown as "CAM=0 Deg" 802, "CAM=5 Deg" 804, and "CAM=10 Deg" 806). In FIG. 8A, the iris pupil is about 3.0 mm. In FIG. 8B, the iris pupil is about 5.0 mm.

Notably, as can also be seen from the MTF curves, there are no cut-offs of the spatial frequency beyond 100 cpd (cycles per degree), which for an IOL with SE (Spherical Equivalent) of 20 D (Diopters), this spatial frequency is approximately 30 cpd.

Example of Multi-Zonal IOL with the Exemplified Freeform-Polynomial Surfaces

In another aspect, a multi-zonal IOL with freeform-polynomial surfaces is disclosed. In some embodiments, the multiple zonal structure includes one or more zonal surfaces defines by Chebyshev-based polynomials while other zonal surfaces are defined by other polynomials (e.g., Zernike and Chebyshev polynomials).

Figure 9:
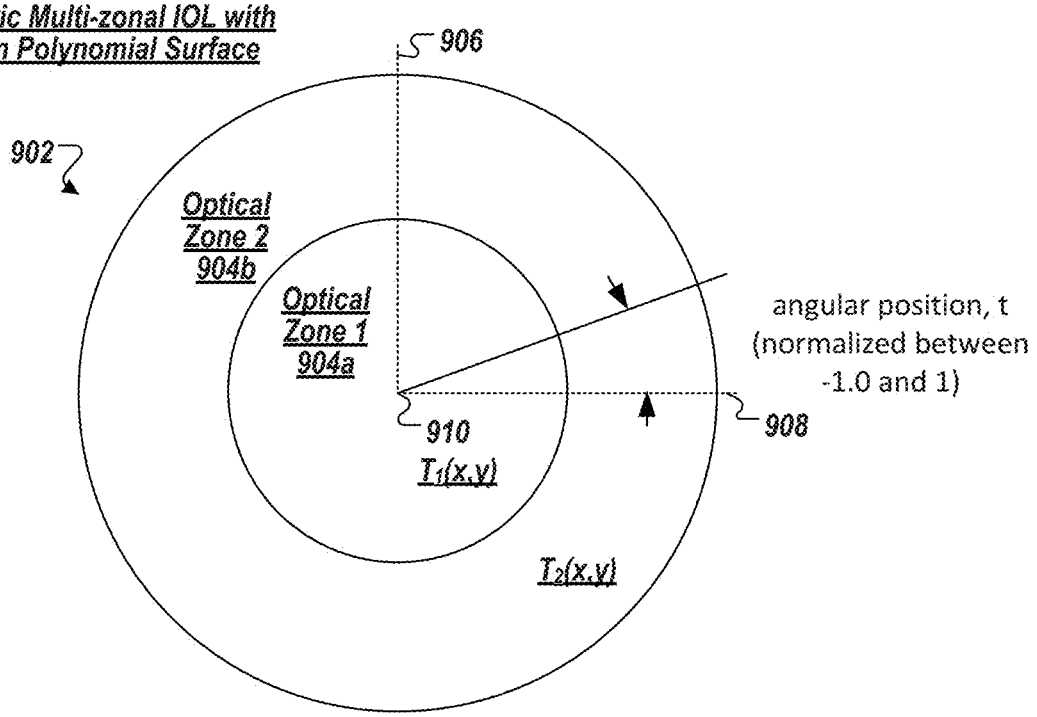
FIG. 9 shows a diagram of a freeform-polynomial surface area (e.g., the second or third height profile) of a second optical zone that symmetrically spans part of the optical face of the apparatus, in accordance with an illustrative embodiment.

In some embodiments, the freeform-polynomial surface area (e.g., the second or third height profile) symmetrically spans part of the optical face of the apparatus). FIG. 9 shows a diagram of a freeform-polynomial surface area (e.g., the second or third height profile) of a second optical zone that symmetrically spans part of the optical face of the apparatus, in accordance with an illustrative embodiment.

As shown in FIG. 9, the ophthalmic apparatus 900 includes an optical face 902 (e.g., the portion of the face surface of the ophthalmic apparatus that include corrective optical structures) that includes the one or more optical zones 904 (shown as "optical zone 1" 904a and "optical zone 2" 904b). The first zone of the optical face has a boundary defined by a first axis 906 of the face and a second axis 908 of the face (e.g., wherein the first axis is orthogonal to the second axis), and each of the x-spatial locations at value −1.0 and at value 1.0 is located at a first radial position along the first axis between a center location 910 of the ophthalmic apparatus and the boundary, and each of the y-spatial locations at value −1.0 and at value 1.0 is located at the first radial position along the second axis between the center location of the ophthalmic apparatus and the boundary. As shown, the "optical zone 1" 904a has a first T(x,y) height profile (e.g., as described in relation to Equation 1) that is superimposed over, e.g., the base or typical aspherical height profile. In some embodiments, the "optical zone 1" 904a has a surfaces defined by other polynomials (e.g., Zernike, or combination of Zernike and Chebyshev polynomials).

In some embodiments, the second "optical zone 2" 904b is characterized by a third height profile $T_2(x,y)$ (e.g., an extra height profile associated with cylinder power) superimposed on a first height profile (e.g. a base or typical aspheric height profile), the third height profile being defined as:

$$T_2(x,y)=\Sigma\{c_2(i_2,j_2)*\cos(i_2*\arccos(t_2))*\cos(j_2*\arccos(t_2))\} \quad \text{(Equation 4)}$$

where $c_2(i_2,j_2)$ is a coefficient based on $i_2$ and $j_2$, which are each integers (e.g., ranging between 0 and 10), x and y are spatial locations on the second freeform-polynomial surface area and has values between −1.0 and 1.0, and $t_2$ is a normalized parameter having values between −1.0 and 1.0 (e.g., associated with the intended correction meridian). In some embodiments, the "optical zone 2" 904b has a surfaces defined by other polynomials (e.g., Zernike, or combination of Zernike and Chebyshev polynomials).

In some embodiments, the freeform-polynomial surface area (e.g., the second or third height profile) asymmetrically spans part of the optical face of the apparatus. That is, the first zone of the optical face has a boundary defined by a first axis of the face and a second axis of the face (e.g., wherein the first axis is orthogonal to the second axis). Each of the x-spatial locations at value −1.0 and at value 1.0 is located at a first radial position along the first axis between a center location of the ophthalmic apparatus and the boundary, and each of the y-spatial locations at value −1.0 and at value 1.0 is located at a second radial position along the second axis between the center location of the ophthalmic apparatus and the boundary, where the first radial position and the second radial position are different.

Figure 10:
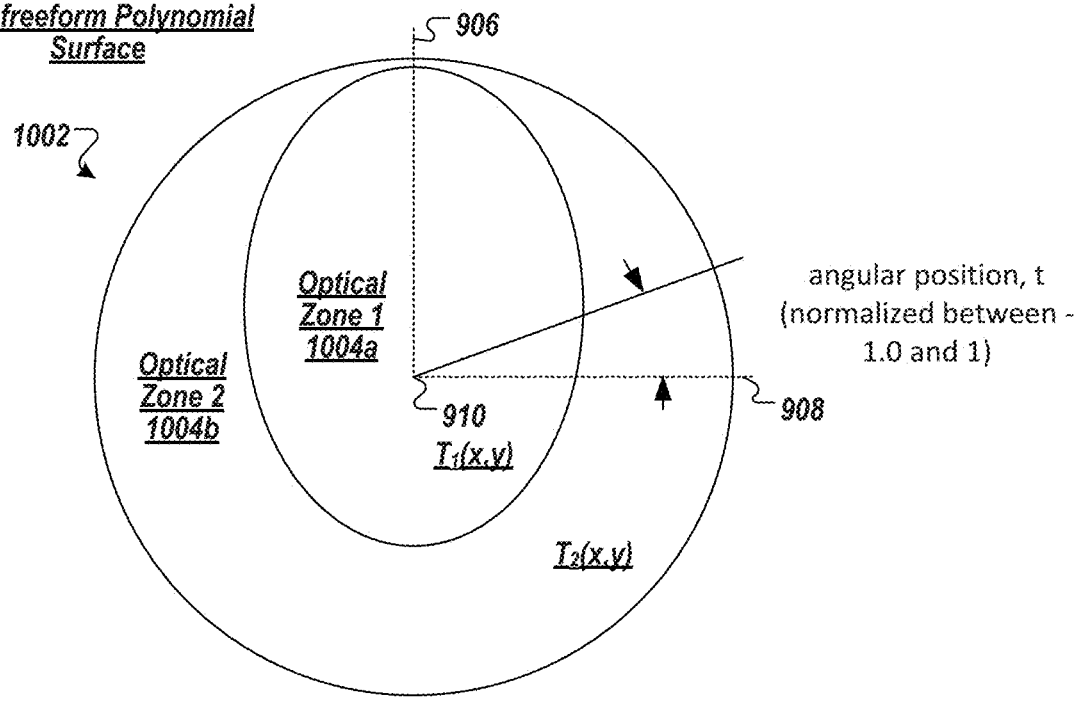
FIG. 10 shows a diagram of a freeform-polynomial surface area (e.g., the second or third height profile) of a second optical zone that symmetrically spans part of the optical face of the apparatus, in accordance with an illustrative embodiment.

FIG. 10 shows a diagram of a freeform-polynomial surface area (e.g., the second or third height profile) of a second optical zone that symmetrically spans part of the optical face of the apparatus, in accordance with an illustrative embodiment.

As shown in FIG. 10, the ophthalmic apparatus 1000 includes the optical face 902 (e.g., the portion of the face surface of the ophthalmic apparatus that include corrective optical structures) that includes the one or more optical zones 1004 (shown as "optical zone 1" 1004a and "optical zone 2" 1004b) that are asymmetric one another. The first zone of the optical face has a boundary defined by a first axis 906 of the face and a second axis 908 of the face (e.g., wherein the first axis is orthogonal to the second axis), and each of the x-spatial locations at value −1.0 and at value 1.0 is located at a first radial position along the first axis between a center location 910 of the ophthalmic apparatus and the boundary, and each of the y-spatial locations at value −1.0 and at value 1.0 is located at the first radial position along the second axis between the center location of the ophthalmic apparatus and the boundary. As shown, the "optical zone 1" 1004a has a first T(x,y) height profile (e.g., as described in relation to Equation 1) that is superimposed over, e.g., the base or typical aspherical height profile. In some embodiments, the "optical zone 1" 1004a has a surfaces defined by other polynomials (e.g., Zernike, or combination of Zernike and Chebyshev polynomials).

In some embodiments, the second "optical zone 2" 1004b is characterized by a third height profile $T_2(x,y)$ (e.g., as described in relation to Equation 3) that are each superimposed over, e.g., the base or typical aspherical height profile. In some embodiments, the "optical zone 2" 904b has a surfaces defined by other polynomials (e.g., Zernike, or combination of Zernike and Chebyshev polynomials).

It is contemplated that other zone shapes may be used for a given zone of the multiple zones. Example of other zone shape include, but not limited to, a rectangle, diamond, and various freeform polygons.

Figure 11:
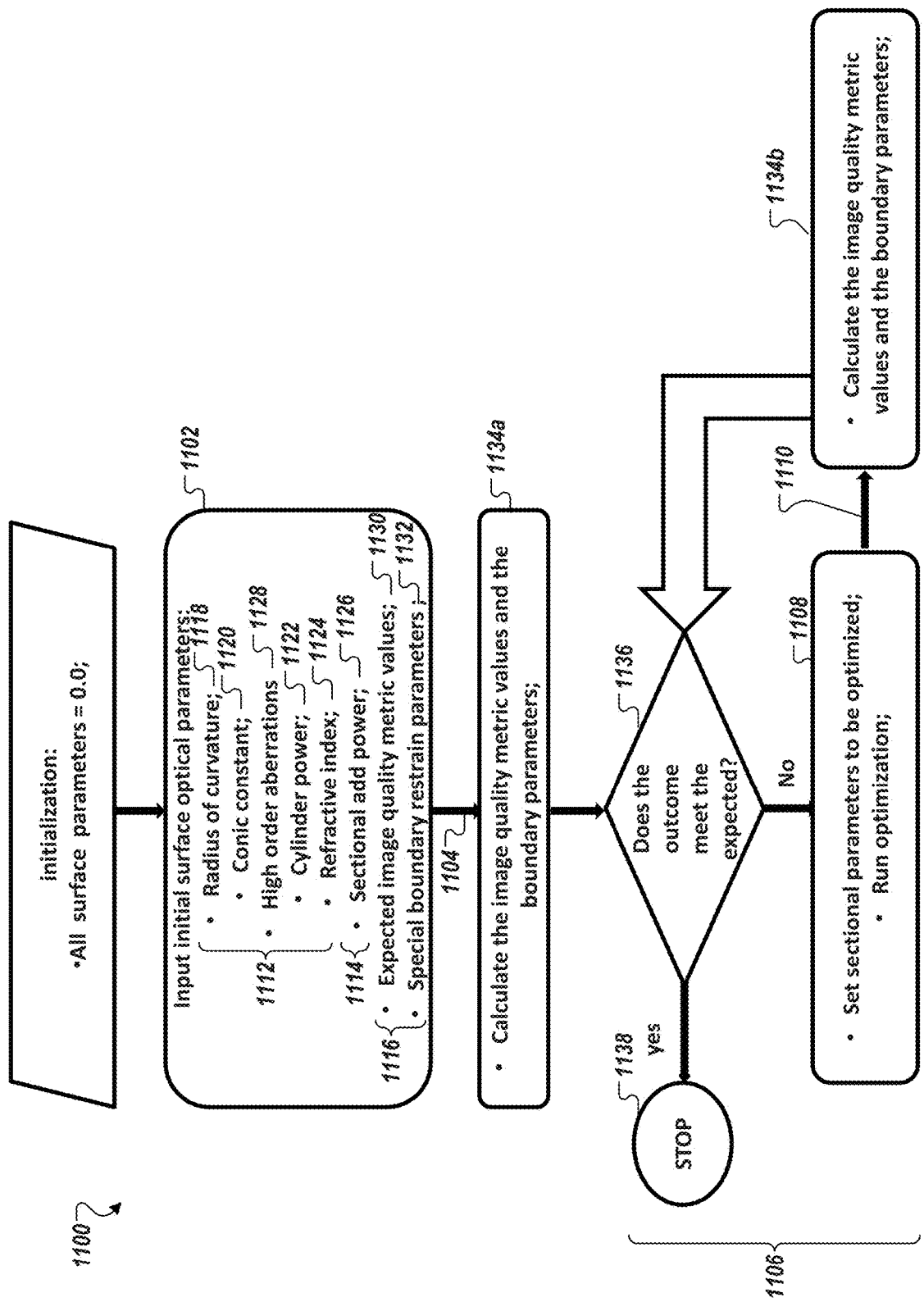
FIG. 11 is diagram of a method to generate the freeform-polynomial surface area of FIG. 1, in accordance with an illustrative embodiment.

FIG. 11 is diagram of a method 1100 to generate, via a processor, the freeform-polynomial surface area of FIG. 1, in accordance with an illustrative embodiment. As shown in FIG. 11, the method 1100 includes generating (1102), via a processor, an initial design (1104) comprising a base surface (with base cylindrical power) and sectional enhancements (with added cylindrical power derived from the Chebyshev-based polynomial expression, Zernike-based polynomial expression) and iteratively generating (1108) and evaluating, a revised design (1110), generated according to an optimization routine (1108) that is performed based on sectional parameters, until pre-defined image quality metric values and boundary parameter are achieved. The sectional enhancements power of the initial design and the iterative design is the ETA polynomial surface of FIG. 1.

Referring still to FIG. 11, the method 1100 includes generating (1102) a first design (1104) via i) initial surface optical parameter, including a) base surface optical parameters 1112 and b) sectional surface optical parameters 1114, and ii) the pre-defined image quality metric values 1116. The base surface optical parameters 1112 include, in some embodiments, parameters associated with a radius of curvature for the toric lens (shown as "Radius of curvature" 1118), parameters associated with conic constant and aspheric coefficients (shown as "Conic constant" 1120), parameters associated with base cylinder power (shown as "Cylinder power" 1122), and parameters associated lens and/or coating material characteristics such as refractive index (shown as "Refractive index" 1124). Other parameters may be used as part of the base surface optical parameters 1112. The section surface optical parameters 1114, in some embodiments, includes parameters associated with sectional added power and meridian characteristics (shown as "Sectional add power" 1128) and parameters associated with high order aberration characteristics, e.g., Zernike aberrations above second-order (shown as "High order aberrations" 1128).

Referring still to FIG. 11, the parameters associated with the sectional added power 1126, in some embodiments, include a mathematical expression comprising a combination of one or more polynomial expressions (e.g., Chebyshev-based polynomial expression, Zernike-based polynomial expression, etc.) each having a distinct complex orders. In some embodiments, the cylindrical power for the added power are all refractive. The parameters associated with the high order aberration characteristics 1128, in some embodiments, include polynomial values (e.g., based on Zernike polynomials, Chebyshev polynomials, and combinations thereof) or characteristics such as polynomial orders and types as well as meridian boundaries for the high order aberrations. The high order aberration is constrained, e.g., from minimum to maximum cylindrical power over one or more meridian sections. In some embodiments, the high order aberrations is constrained or designated to a meridian, e.g., that corresponds to a corneal irregular geometry or limited retinal area functions. In other embodiments, the high order aberrations may be introduced as weights a freeform polynomial weights to form the freeform-polynomial surface area. In such embodiments, the high order aberrations and its meridian locations on the lens surface may be optimized prior to the freeform polynomial weights being determined to facilitate a customized design that is tailored for a given patient (i.e., particularly in view of corneal irregular geometry or limited retinal area functions). Such customization has a potential to truly benefit patients having cornea with or without astigmatism, patients with local Keratoconus with or without astigmatism, patients with glaucoma, patients with retinal macular degeneration (AMD), and the like.

Referring still to FIG. 11, the parameters associated with the pre-defined image quality metric value 1116 includes parameters associated with expected image quality metric (shown as "Expected image quality metric values" 1130) and parameters associated with special boundary restrain parameters (shown as "Special boundary restrain parameters" 1132). In some embodiments, image quality metric is based a comparison of a base polychromatic diffraction MTF (modular transfer function) (e.g., tangential and sagittal) to a number of error polychromatic diffraction MTFs values, e.g., where one or more polychromatic diffraction MTFs are determined for one or more misalignments of the generated toric lens from its intended operating meridians, e.g., at 5-degree misalignment and at 10-degree misalignment.

Referring still to FIG. 11, the initial design (1104) is evaluated (1134a) to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, e.g., as shown in FIGS. 8A and 8B. The determined image quality metric values are evaluated (1136) to determine whether the image quality metric values and boundary parameters meet an expected outcome, e.g., a value of 0.2 (MTF). In some embodiments, the expected outcome is whether there is no cut off through spatial frequency beyond 100 cpd. Upon determining that the condition is met, the method 1100 is stop (1138). It is contemplated that other image quality metrics may be used, e.g., the optical transfer function (OTF), phase transfer function (PhTF), and etc.

Where the condition is not met, the method 1100 adjusts (1108) sectional parameters to be optimized and rerun the optimization to generate the revised design 1110. The adjusted sectional parameters may include adjusting values for i and j of the Chebyshev or Zernike polynomials, as discussed in reference to Equation 1 or Equation 2. In some embodiments, only one value of i or j of the Chebyshev or Zernike polynomials is adjusted to generate each design variant. In other embodiments, the values of i and j of the Chebyshev or Zernike polynomials are adjusted concurrently.

Referring back to FIG. 11, the method 1100 then includes evaluating (1334b) the revised design 1110 to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, as discussed in relation to step 1134a, and re-evaluating (1136) whether the revised image quality metric values and boundary parameters meet the expected outcome, as discussed in relation to step 1136.

In some embodiments, the method 1100 is performed in an optical and illumination design tool such as Zemax (Kirkland, Wash.). It is contemplated that the method 1100 can be performed in other simulation and/or design environment.

The present technology may be used, for example, in the Tecnis toric intraocular lens product line as manufactured by Abbott Medical Optics, Inc. (Santa Ana, Calif.).

It is not the intention to limit the disclosure to embodiments disclosed herein. Other embodiments may be used that are within the scope and spirit of the disclosure. In some embodiments, the above disclosed angularly varying phase members may be used for multifocal toric, extended range toric, and other categorized IOLs for extended tolerance of astigmatism caused by factors including the cylindrical axis misalignment. In addition, the above disclosed angularly varying phase members may be applied to spectacle, contact lens, corneal inlay, anterior chamber IOL, or any other visual device or system.

Exemplary Computer System

Figure 12:
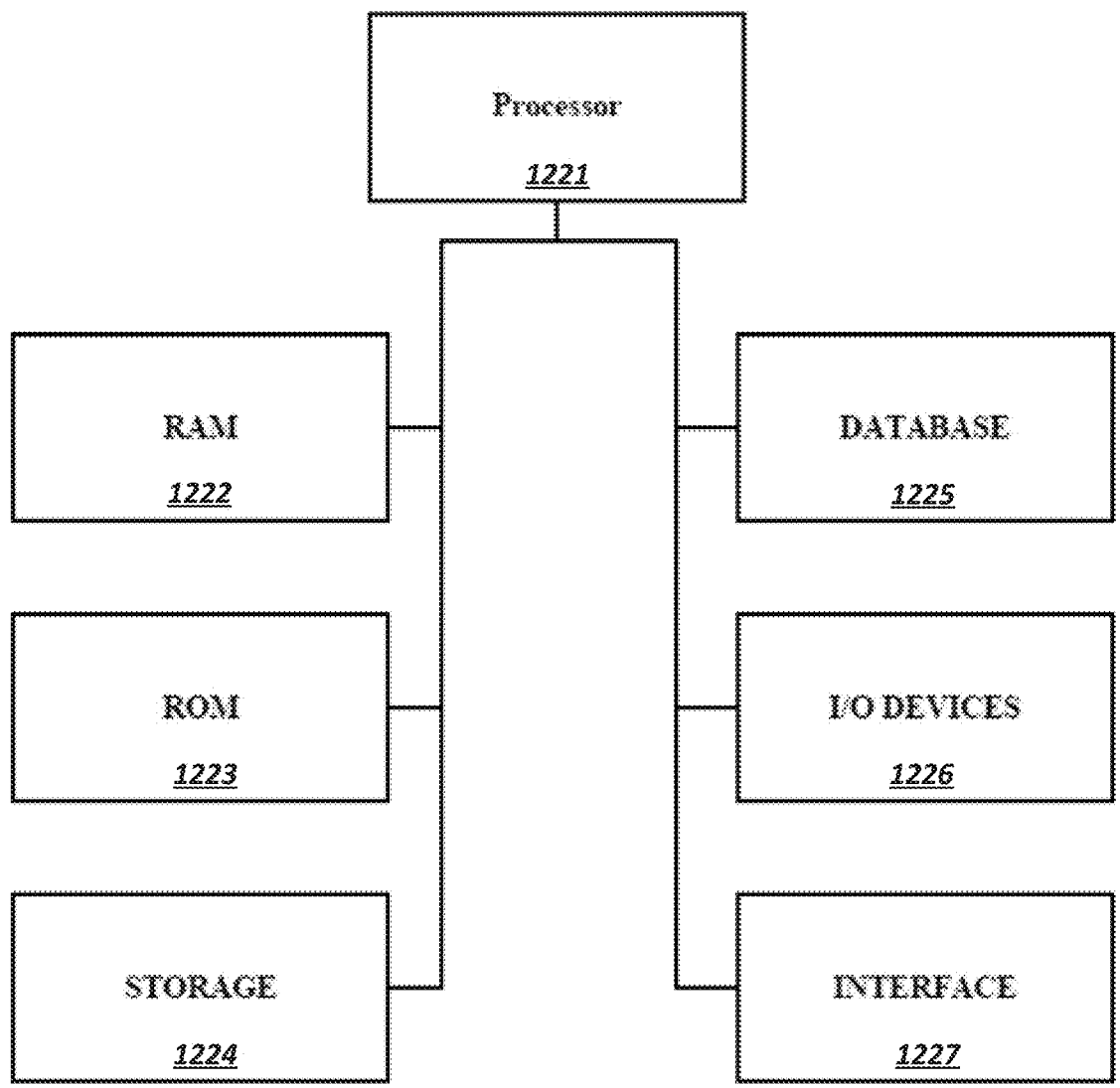
FIG. 12 is a diagram of an example computing device configured to generate the freeform-polynomial surface area disclosed herein.

FIG. 12 is a diagram of an example computing device configured to generate the polynomial surface disclosed herein. As used herein, "computer" may include a plurality of computers. The computers may include one or more hardware components such as, for example, a processor 1221, a random access memory (RAM) module 1222, a read-only memory (ROM) module 1223, a storage 1224, a database 1225, one or more input/output (I/O) devices 1226, and an interface 1227. Alternatively and/or additionally, controller 1220 may include one or more software components such as, for example, a computer-readable medium including computer executable instructions for performing a method associated with the exemplary embodiments. It is contemplated that one or more of the hardware components listed above may be implemented using software. For example, storage 1224 may include a software partition associated with one or more other hardware components. It is understood that the components listed above are exemplary only and not intended to be limiting.

Processor 1221 may include one or more processors, each configured to execute instructions and process data to perform one or more functions associated with a computer for indexing images. Processor 1221 may be communicatively coupled to RAM 1222, ROM 1223, storage 1224, database 1225, I/O devices 1226, and interface 1227. Processor 1221 may be configured to execute sequences of computer program instructions to perform various processes. The computer program instructions may be loaded into RAM 1222 for execution by processor 1221. As used herein, processor refers to a physical hardware device that executes encoded instructions for performing functions on inputs and creating outputs.

RAM 1222 and ROM 1223 may each include one or more devices for storing information associated with operation of processor 1221. For example, ROM 1223 may include a memory device configured to access and store information associated with controller 1220, including information associated with IOL lenses and their parameters. RAM 1222 may include a memory device for storing data associated with one or more operations of processor 1221. For example, ROM 1223 may load instructions into RAM 1222 for execution by processor 1221.

Storage 1224 may include any type of mass storage device configured to store information that processor 1221 may need to perform processes consistent with the disclosed embodiments. For example, storage 1224 may include one or more magnetic and/or optical disk devices, such as hard drives, CD-ROMs, DVD-ROMs, or any other type of mass media device.

Database 1225 may include one or more software and/or hardware components that cooperate to store, organize, sort, filter, and/or arrange data used by controller 1220 and/or processor 1221. For example, database 1225 may store hardware and/or software configuration data associated with input-output hardware devices and controllers, as described herein. It is contemplated that database 1225 may store additional and/or different information than that listed above.

I/O devices 1226 may include one or more components configured to communicate information with a user associated with controller 1220. For example, I/O devices may include a console with an integrated keyboard and mouse to allow a user to maintain a database of images, update associations, and access digital content. I/O devices 1226 may also include a display including a graphical user interface (GUI) for outputting information on a monitor. I/O devices 1226 may also include peripheral devices such as, for example, a printer for printing information associated with controller 1220, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1227 may include one or more components configured to transmit and receive data via a communication network, such as the Internet, a local area network, a workstation peer-to-peer network, a direct link network, a wireless network, or any other suitable communication platform. For example, interface 1227 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

What is claimed is:

1. An ophthalmic apparatus having regions of one or more base spherical powers and one or more cylinder powers that are added to the one or more base spherical power for correcting an astigmatism, the apparatus comprising one or more optical zones, including a first optical zone defined by a freeform-polynomial surface area, wherein light incident to a first region of the freeform-polynomial surface area, and regions nearby to the first region, is directed to a first point of focus such that the regions nearby to the first region direct light to the first point of focus when the freeform-polynomial surface area is rotationally offset from the first region, thereby establishing a band of operational meridian for the apparatus to an intended correction meridian, and wherein the freeform-polynomial surface area is defined as a mathematical expression comprising a combination of one or more polynomial expressions each having a distinct complex orders, wherein the freeform-polynomial surface area has a second height profile $T(x,y)$ on a first base height profile, the second height profile being defined as:

$$T(x,y)=\Sigma\{c(i,j)*\cos(i*\arccos(t))*\cos(j*\arccos(t))\}$$

where $c(i,j)$ is a coefficient based on i and j, which are each orders of the polynomial and expressed as integers, x and y are spatial locations on the freeform-polynomial surface area, and t is a normalized parameter having values between −1.0 and 1.0, wherein the ophthalmic apparatus comprises a rotationally-tolerant intraocular lens (IOL).

2. The ophthalmic apparatus of claim 1, wherein at least one of the one or more polynomial expression is selected from the group consisting of a Chebyshev polynomial and a Zernike polynomial.

3. The ophthalmic apparatus of claim 1, wherein the freeform-polynomial surface area establishes the band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

4. The ophthalmic apparatus of claim 1, wherein the freeform-polynomial surface area has the second height profile $T(x,y)$ in which i has an order of 0 to at least 6 and j has an order of 0 to 6.

5. The ophthalmic apparatus of claim 1, wherein the ophthalmic apparatus comprises an optical face that includes the one or more optical zones, the optical face having a boundary defined by a first axis of the face and a second axis of the face and x-spatial locations and y-spatial locations, and
    wherein each of the x-spatial locations at value −1.0 and at value 1.0 coincides with, or is near, the boundary, and each of the y-spatial locations at value −1.0 and at value 1.0 coincides with, or is near, the boundary.

6. The ophthalmic apparatus of claim 1, wherein the ophthalmic apparatus comprises an optical face that includes the one or more optical zones, the optical face having a boundary defined by a first axis of the face and a second axis of the face, and
    wherein each of the x-spatial locations at value −1.0 and at value 1.0 is located at a first radial position along the first axis between a center location of the ophthalmic apparatus and the boundary, and
    wherein each of the y-spatial locations at value −1.0 and at value 1.0 is located at the first radial position along the second axis between the center location of the ophthalmic apparatus and the boundary.

7. The ophthalmic apparatus of claim 1, wherein the ophthalmic apparatus comprises an optical face that includes the one or more optical zones, the optical face having a boundary defined by a first axis of the face and a second axis of the face, and wherein each of the x-spatial locations at value −1.0 and at value 1.0 is located at a first radial position along the first axis between a center location of the ophthalmic apparatus and the boundary, and wherein each of the y-spatial locations at value −1.0 and at value 1.0 is located at a second radial position along the second axis between the center location of the ophthalmic apparatus and the boundary, wherein the first radial position and the second radial position are different.

8. The ophthalmic apparatus of claim 1, wherein the freeform-polynomial surface area has for each continuously distributed contour line at the IOL plane a difference of less than about 0.6 Diopters.

9. The ophthalmic apparatus of claim 1, wherein the one or more optical zones includes a second optical zone defined by a second freeform-polynomial surface region, wherein the second freeform-polynomial surface area is characterized and defined by a second polynomial.

10. The ophthalmic apparatus of claim 9, wherein the second freeform-polynomial surface area has a second height profile that varies according to a freeform polynomial selected from the group consisting of a Chebyshev polynomial and a Zernike polynomial.

11. The ophthalmic apparatus of claim 9, wherein light incident to a second region of the second freeform-polynomial surface area, and regions nearby to the second region, is directed to a second point of focus such that the regions nearby to the second region direct light to the second point of focus when the second freeform-polynomial surface area is rotationally offset from the second region.

12. The ophthalmic apparatus of claim 9, wherein light incident to a second region of the second freeform-polynomial surface area, and regions nearby to the second region, is directed to the first point of focus such that the regions nearby to the second region direct light to the first point of focus when the second freeform-polynomial surface area is rotationally offset from the second region.

13. The ophthalmic apparatus of claim 9, wherein the second freeform-polynomial surface area has a third height profile $T_2(x,y)$ superimposed on a first height profile, the third height profile being defined as:

$$T_2(x,y)=\Sigma\{c_2(i_2,j_2)*\cos(i_2*\arccos(t_2))*\cos(j_2*\arccos(t_2))\}$$

where $c_2(i,j)$ is a coefficient based on $i_2$ and $j_2$, which are each integers, x and y are spatial locations on the second freeform-polynomial surface area and has values between −1.0 and 1.0, and $t_2$ is a normalized parameter having values between −1.0 and 1.0.

14. The ophthalmic apparatus of claim 9, wherein the second freeform-polynomial surface area comprise a monofocal lens, a bifocal lens, or a multi-focal lens.

15. The ophthalmic apparatus of claim 9, wherein the second freeform-polynomial surface area comprise an extended range of vision lens.

16. The ophthalmic apparatus of claim 1, wherein the one or more optical zones includes a second optical zone defined by a second freeform-polynomial surface region, wherein the second freeform-polynomial surface area is characterized and defined by a second combination of one or more polynomial expressions each having a distinct complex orders.

17. The ophthalmic apparatus of claim 16, wherein at least one of the one or more polynomial expression is selected from the group consisting of a Chebyshev polynomial and a Zernike polynomial.

18. The ophthalmic apparatus of claim 1, wherein the freeform-polynomial surface area comprise is on a monofocal lens, a bifocal lens, or a multi-focal lens.

19. The ophthalmic apparatus of claim 1, wherein the freeform-polynomial surface area is on an extended range of vision lens.

20. The ophthalmic apparatus of claim 1, wherein the freeform-polynomial surface area comprises refractive surfaces.

21. The ophthalmic apparatus of claim 1, wherein the freeform-polynomial surface area comprises diffractive surfaces.

22. The ophthalmic apparatus of claim 1, wherein the coefficients c(i,j) are optimized to place accumulated high surface amplitude to non-functional retinal area.

23. The ophthalmic apparatus of claim 1, wherein the coefficients c(i,j) are optimized to account for irregular corneal shape.

* * * * *